United States Patent [19]

Hofmann

[11] 4,237,903

[45] Dec. 9, 1980

[54] QRS DETECTOR FOR EKG SIGNALS

[75] Inventor: Gerhard H. Hofmann, Freiburg im Breisgau, Fed. Rep. of Germany

[73] Assignee: Hellige GmbH, Freiburg im Breisgau, Fed. Rep. of Germany

[21] Appl. No.: 8,029

[22] Filed: Jan. 31, 1979

[51] Int. Cl.³ .............................................. A61B 5/04
[52] U.S. Cl. ................................................. 128/708
[58] Field of Search ............... 128/696, 708, 901, 902, 128/702, 703, 704, 705, 706

[56] References Cited

U.S. PATENT DOCUMENTS

| 3,174,478 | 3/1965 | Kahn ................................... 128/706 |
| 3,572,324 | 3/1971 | Petersen ............................... 128/706 |
| 3,675,643 | 7/1972 | Funfstuck et al. ................... 128/706 |
| 3,750,644 | 7/1973 | Ragsdale ............................. 128/706 |
| 3,998,214 | 12/1976 | Garrison ............................. 128/702 |

*Primary Examiner*—William E. Kamm

[57] ABSTRACT

An improves QRS detector is disclosed which utilizes a comparison between the arithmetic mean value of the filtered and full wave rectified EKG signal and such EKG signal reduced by a proportionality factor related to the ratio between the peak and mean value of a full wave rectified sinusoidal wave form. An adaptive threshold circuit is additionally disclosed which serves to increase the threshold value to the amplitude of detected QRS complexes.

11 Claims, 14 Drawing Figures

QRS DETECTOR FOR EKG SIGNALS

BACKGROUND OF THE INVENTION

1. Field of the Invention

This invention relates generally to the processing of biologically generated signals and particularly to detectors of the type used to identify QRS complexes and other periodic wave forms in signals, such as electrocardiograms, commonly known as EKG signals, developed during the monitoring of living beings. Such QRS detectors find particular usefulness in heart rate monitors and similar equipment, such as controlled defibrillators, demand pacemakers, and devices synchronized to heart activity for performing injections or assisting circulation.

2. Description of the Prior Art

QRS detectors are typically used to identify QRS complexes in the presence of other biological and equipment generated signals, such as P and T waves and sinusoidal noise, such as AC line voltage noise. In heart rate monitors, the detected QRS complexes are then processed by counting or other techniques to determine the heart rate. Such monitors normally include electrodes and an amplifier for detecting the EKG; a high pass filter for enhancing the QRS complexes while minimizing the lower frequency P and T waves; a QRS detector; a pulse shaper for generating a fixed width pulse when a QRS complex is detected; and a pulse counter, together with recording and/or alarm equipment.

Conventional QRS detectors generate an output indicating the presence of a QRS complex whenever the amplitude of the filtered EKG signal exceeded the threshold value. The threshold values were originally manually selected by the technician operating the heart rate monitoring equipment and then automatic threshold circuitry was developed for generating a threshold value related to the amplitude of the filtered EKG signal. The threshold value generated in this manner was affected by changes of the polarity of the QRS complex. Full wave rectifiers were then added to the equipment, in the signal processing before the QRS detection, to avoid polarity dependence. Amplitude selection circuitry is sometimes used to filter out pulses generated by pacemakers and similar equipment.

QRS detectors with automatic threshold value generating circuitry have conventionally used a capacitor-resistor network in an integrating mode to store a slowly decaying threshold voltage value derived from the filtered and/or rectified EKG signal and transistor switching circuitry or a comparator for generating an output signal whenever the instantaneous value of the EKG signal exceeded the slowly changing threshold value stored across the capacitor. Such QRS detectors provided improved recognition of QRS complexes, particularly during circumstances of chaning QRS complex amplitudes caused, for example, by changes in quality of the connections between the electrodes and the body.

Conventional QRS detectors as described above are, unfortunately, not always able to distinguish between QRS complexes and noise, particularly sinusoidal noise, such as that caused by the AC line voltage. An improved QRS detector is shown in German published patent application DE-OS 25 45 802, Heart Signal Discriminator, which has been designed to discriminate between QRS complexes and AC noise. This circuit operates by generating a threshold value equal to the mean value of the amplitude of the EKG signal and then compares the instantaneous EKG signal against this threshold value. An output signal is then generated whenever the peak value of the instantaneous EKG signal exceeds the mean value by a predetermined amount. Such QRS detectors are still susceptible to error induced by AC noise, particularly during variations in the amplitude of the QRS complexes. For example, the threshold value may become too large to indicate the presence of QRS complexes when such signals are weak.

SUMMARY OF THE INVENTION

An improved QRS detector with automatic threshold generating circuitry is disclosed which is capable of discriminating between QRS complexes and AC noise in an EKG signal, even under conditions of varying amplitudes of the QRS complexes. A threshold value is automatically generated equal to the arithmetic means value of the EKG signal. The EKG signal is then reduced by an appropriate ratio, before it is compared to the threshold value, so that the reduced value exceeds the threshold for true QRS complexes, but not for AC noise signals. An appropriate reduction factor, K, is the ratio between the arithmetic average value of a full wave rectified AC voltage and its peak value, i.e. approximately 1.57 to 1. In this manner, the detector discriminates against sinusoidal noise in favor of QRS complexes on the basis that the ratio of peak to average value of the triangular shaped QRS complexes will be higher than the ratio of peak to average value of the sinusoidal noise.

In an alternate embodiment of the invention, a feedback loop is disclosed which adapts the threshold value as a function of the output of the QRS detector to minimize sensitivity to changes in the amplitudes of the QRS complexes.

DETAILED DESCRIPTION OF THE PREFERRED EMBODIMENTS

Figure 1:
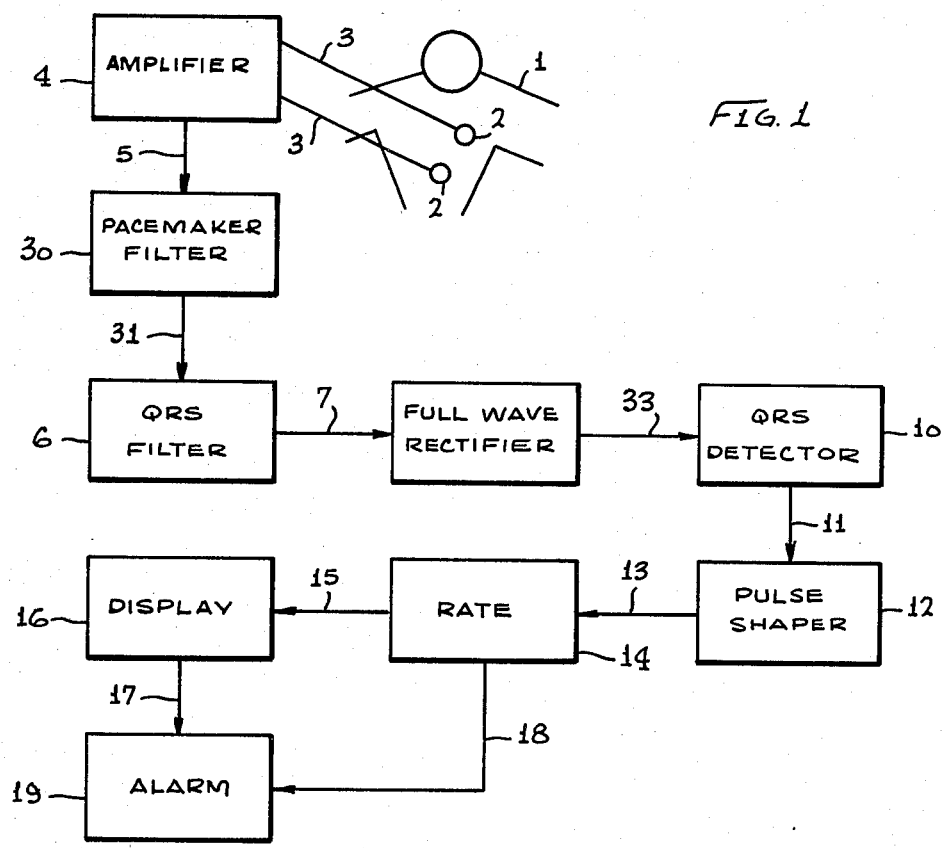
FIG. 1 is a block diagram of a preferred embodiment of a heart rate monitor in accordance with the instant invention.
Figure 2A:
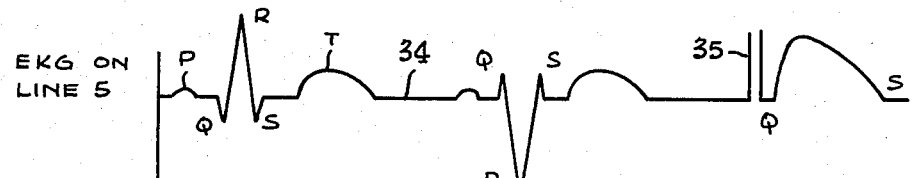
FIGS. 2(a) through 2(d) are a series of graphs of representative signal wave forms appearing in the heart rate monitor of FIG. 1.
Figure 2B:
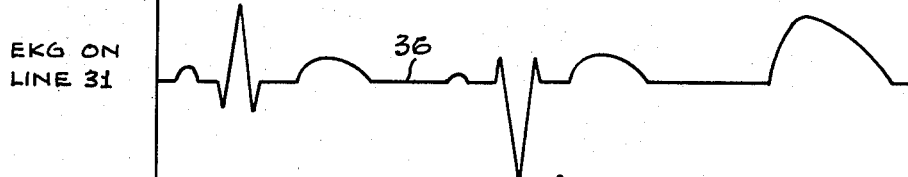

A heart rate monitor, in accordance with the instant invention, is shown in FIG. 1, in which electrodes 2 are positioned on living body 1 in accordance with conventional practice. Electrodes 2 are connected to amplifier 4 via cables 3 in order to produce a conventional EKG signal on line 5. FIG. 2a is a graph of EKG 34 on line 5 and shows P, Q, R, S and T complexes in the conventional manner. Pacemaker filter 30 may be provided, if required, to remove undesired pulses from EKG 34, such as pacemaker spike 35. FIG. 2b shows EKG 36 on line 31 after the removal of pulse 35.

Figure 2C:
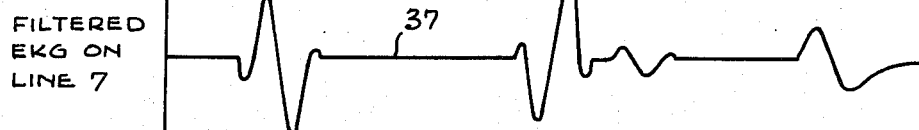

A high pass filter, such as QRS filter 6, receives EKG 36 via line 31. This filter is utilized to enhance the QRS complexes, which contain high frequency components, and minimize the P and T waves which contain lower frequency components. Filtered EKG signal 37, having QRS complexes enhanced, is shown in FIG. 2c as it appears on output 7 of QRS filter 6.

Figure 2D:
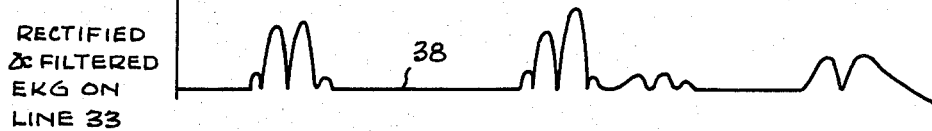

Full wave rectifier 32 may then be utilized to avoid complications resulting from changes in polarity of the QRS complex in the EKG signal, as illustrated in the first two complexes present in FIG. 2b. FIG. 2d shows filtered and rectified EKG 38 as it appears on output 33 of rectifier 32.

Figure 5:
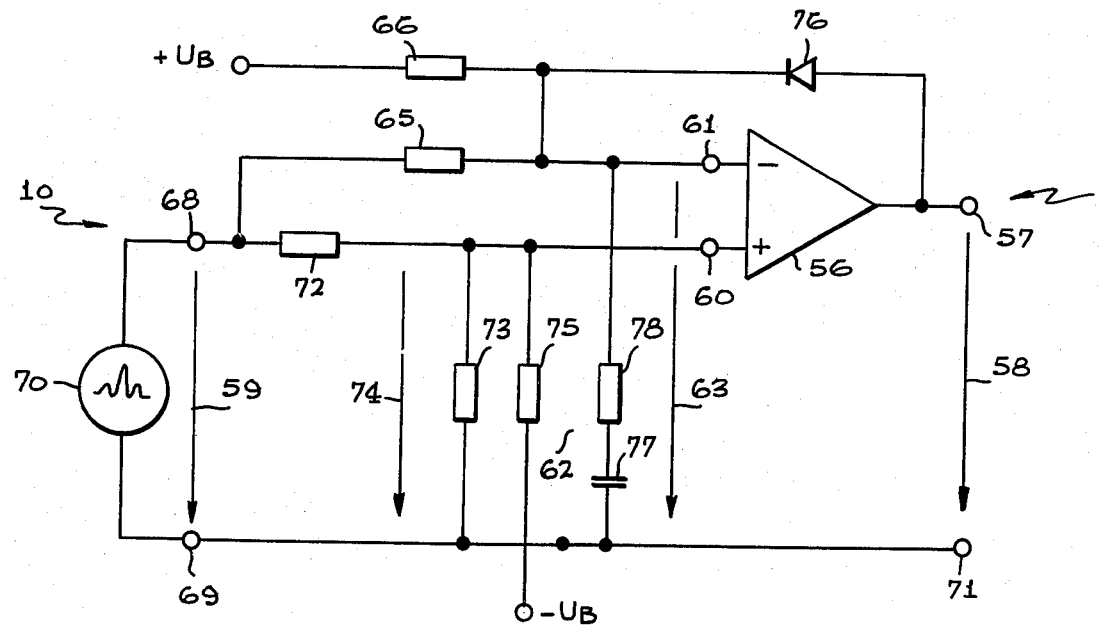
FIG. 5 is an alternate embodiment of QRS detector 10.

Filtered and rectified EKG 38 is then applied to QRS detector 10 in order to generate a pulse whenever a QRS complex is detected. Detector 10 thereby serves to produce a pulse once per heartbeat. These pulses are applied to pulse shaper 12 via line 11 in order to generate a standard width pulse for ease in further processing and to minimize the effects of more than one output pulse from detector 10 during the same heartbeat, as the result of, for example, the full wave rectification. See EKG 38 as shown in FIG. 2d. Schematic diagrams of preferred embodiments of QRS detector 10 are shown in FIGS. 3 and 5 herein below.

Figure 3:
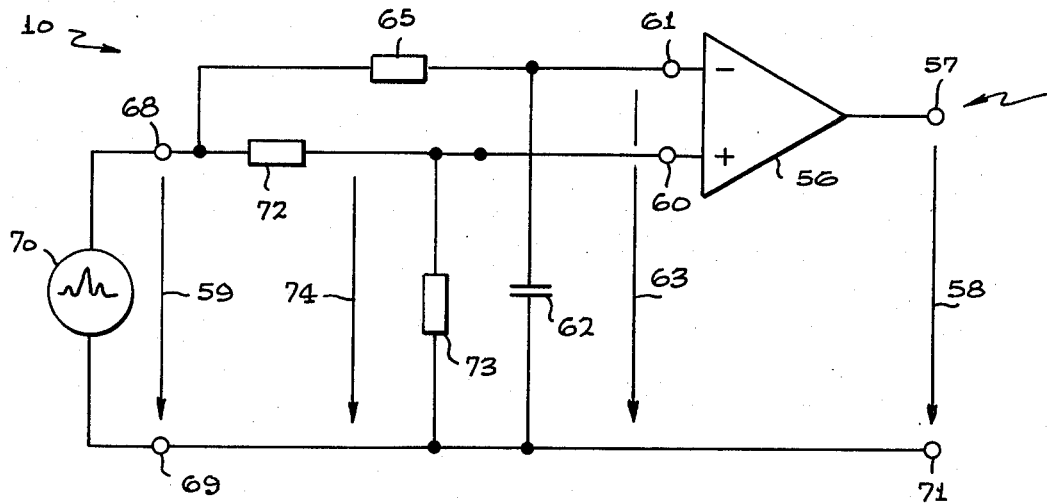
FIG. 3 is a schematic diagram of QRS detector 10 in accordance with a first embodiment of the instant invention.

FIG. 3 is a schematic diagram of a first embodiment of detector 10 shown in FIG. 1. Detector 10 is basically a comparison circuit which is able to distinguish between noise resulting from AC line voltage and desired signals resulting from the EKG. In accordance with the instant invention, comparison is made between an automatically generated threshold value and a signal related to the EKG. The threshold value is derived as an average value, such as the arithmetic mean value, of the input signal. In accordance with this invention, this threshold value is compared to the EKG signal from which it is derived after the EKG signal has been reduced by factor K. The determination of factor K is a key to the instant invention. QRS complexes are generally triangular in shape as opposed to AC line voltage noise, which is sinusoidal. The arithmetic mean value of sinusoidal pulses after full wave rectification is typically higher than the arithmetic mean value of QRS complexes after filtering and full wave rectification. When the EKG signal is reduced by this factor, the amplitude of the EKG during conditions of sinusoidal noise is slightly lower than the threshold value, which is the arithmetic mean value of the input. Proportionality factor K may then easily be calculated. It is well known that the ratio between the arithmetic mean value of full wave rectified sinusoidal wave forms and their peak amplitude is approximately 1 to 1.57. An output signal is then generated whenever the EKG signal, after reduction by this factor, exceeds its arithmetic mean value. This will occur only for QRS complexes. Thus detector 10 discriminates against noise by differentially suppressing sinusoidal signals with respect to triangular signals in an input pulse train.

The details of operation of detector 10 may be conveniently understood from FIG. 3 with reference to the graphs of FIG. 4. Filtered and rectified EKG 38, shown in FIG. 2d, is represented in FIG. 3 as signal 70 and is applied to inputs 68 and 69 of detector 10. This signal is shown as wave form 59 in FIG. 4a and includes, at the leftmost side of the graph, signals 59a which represent sinusoidal noise. The remaining portion of wave form 59 represents filtered and rectified QRS complexes. As discussed above, it is necessary to generate a signal representing the arithmetic mean value of the input wave form 59 and another signal representing input 59 reduced by the appropriate predetermined factor K. Resistor 65 and capacitor 62 serve as a low pass filter, which has an integration time constant of approximately 1 period of a QRS signal, to generate threshold 63. Threshold 63, as shown in FIG. 4a and 4b, is applied to negative input 61 of operational amplifier 56. Resistors 72 and 73 serve as a simple voltage divider, yet provide the critical noise reduction function. Voltage wave form 74, as shown in FIG. 4b, is developed across resistor 73 and applied to the positive input 60 of operational amplifier 56. Voltage 74 is, therefore, proportional to wave form 59 by proportionality factor K.

Figure 4A:
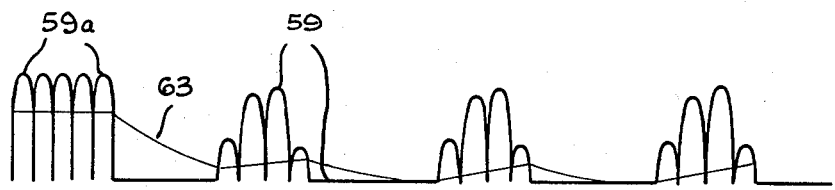
FIGS. 4(a) through 4(d) are a series of graphs of representative signal wave forms of the circuitry shown in FIG. 3.
Figure 4B:
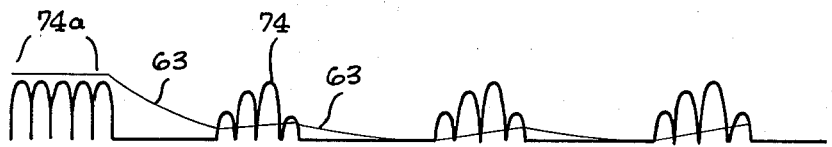

As shown in FIG. 4a, threshold wave form 63 represents the arithmetic mean value of input signal 59, and as such is exceeded by both the AC noise represented by wave form 59a and the QRS complexes. As shown, however, in FIG. 4b, when wave form 59 is reduced by the appropriate factor K AC line noise 74a in FIG. 4b is smaller than threshold value 63, so that no output is developed.

Figure 4C:
Figure 4D:
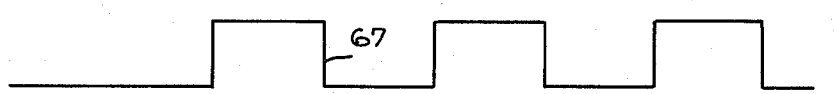

Output pulses 58, appearing between detector outputs 57 and 71, are shown in FIG. 4c. During the occurrence of QRS complex 74 in FIG. 4b, output pulses 58 are generated because the peaks of EKG 59, when reduced by factor K, are still of larger magnitude than the arithmetic mean value, represented by threshold value 63. In this manner, as shown in FIG. 4c, pulses 58 are generated in response to QRS complexes. FIG. 4d is a graphical representation of the output of pulse shaper 12 of FIG. 1 on line 13. The width of pulses 67 is chosen to be sufficiently long so that the multiple peaks of wave form 74 generate only one output pulse 67. Pulse shaper 12 may conveniently be a one-shot multivibrator. Therefore in accordance with the instant invention, an output pulse representing the heart activity of the living body being measured is generated in response to QRS complexes but not in response to AC line voltage noise.

Figure 6A:
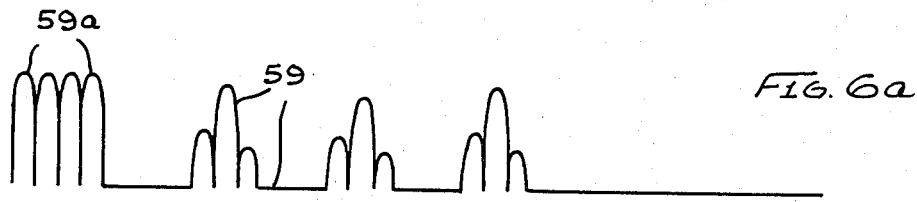
FIGS. 6(a) through 6(c) are a series of graphs of representative signal wave forms of the circuitry shown in FIG. 5.
Figure 6B:
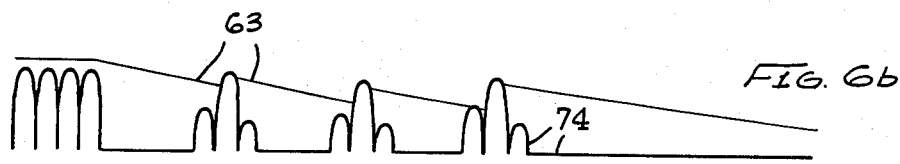
Figure 6C:
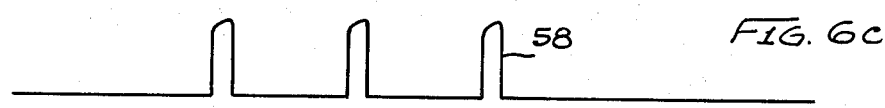

An alternate embodiment of the QRS detector 10 is shown in FIG. 5. Signal 70, when applied to inputs 68 and 69, is shown as wave form 59 in FIG. 6a in which noise 59a represents AC line voltage noise. Resistors 72 and 73 cooperate in the manner described above as a voltage divider to produce signal 74 shown in FIG. 6b, which is the same as wave form 59 after reduction by factor K. However, capacitor 62 of FIG. 3 is replaced by a series combination of resistor 78 and capacitor 77. Input resistor 65 performs the same function as in the embodiment shown in FIG. 3. However, diode 76, connected between output 57 and input 61 of operational amplifier 56, serves to maintain the threshold value at a higher level, as shown in FIG. 6b. Threshold value 63 is increased whenever output wave form 58 is more then the diode drop above the input voltage at input 61. In this manner, as shown in FIG. 6c, only one output pulse 58 is generated as a result of a QRS complex 74. Diode 76 therefore operates to adapt the amplitude of the threshold value to make detector 10 relatively insensitive to changes in QRS complex amplitudes.

In order to complement this noise descrimination effect, QRS detector 10, as shown in FIG. 5, may be provided with circuitry for providing a minimum threshold value. For this purpose, alternatively, resistor 66 may be connected between input 61 and a positive voltage $+U_B$, or the voltage at terminal 60 may be lowered by the use of resistor 75 connected between positive input 60 and negative voltage supply terminal $-U_B$.

I claim:

1. A detector for detecting biologically generated periodic wave form complexes in the presence of sinusoidal noise, comprising:
   automatic threshold means for generating a threshold value signal related to the arithmetic mean value of an input signal;
   comparison means for generating an output signal indicating the presence of the biologically generated wave form complexes whenever the amplitude of a first signal exceeds the threshold value signal; and
   noise reduction means for reducing the first signal relative to the input signal by a proportionality factor such that the amplitude of sinusoidal noise in said first signal is less than the threshold value signal.

2. The detector of claim 1 wherein the automatic threshold means includes a low pass filter.

3. The detector of claim 2 wherein the low pass filter has an integration time constant of approximately one period of the biologically generated periodic wave form complexes.

4. The detector of claim 1 wherein the proportionality factor is related to the ratio between the peak value and the arithmetic mean value of a full wave rectified sinusoidal wave form.

5. The detector of claim 4 wherein the proportionality factor is approximately 1 to 1.57.

6. The detector of claim 1 wherein the comparison means includes a differential operational amplifier and the detector further comprises:
   minimum threshold means for applying an additional bias to the appropriate input of the differential operational amplifier.

7. The detector of claim 1 wherein the automatic threshold means includes amplitude adaptive means for increasing the threshold value in response to an output from the comparison means.

8. The detector of claim 1 wherein:
   the detector includes signal processing means including a high pass filter and a full wave rectifier;
   the automatic threshold means includes a low pass filter and a diode for increasing the threshold value in response to an output from the comparison means;
   the comparison means is a differential operational amplifier wherein the diode is connected between the output and the negative input thereof; and
   the noise reduction means is a voltage divider, the ratio between the output and input of which is the proportionality factor and is equal to the ratio of the peak value to the arithmetic average value of a full wave rectified sinusoidal wave form.

9. An apparatus for detecting biologically-generated wave-form complexes in the presence of sinusoidal noise, comprising:
   means for automatically generating a threshold signal from the arithmetic mean of an input signal;
   means for determining a proportionality factor from the arithmetic mean; and
   means for applying the proportionality factor to said input signal to form a proportioned signal so that sinusoidal noise is differentially suppressed relative to biologically-generated wave-form complexes.

10. The apparatus as defined in claim 9, including:
    means for comparing said proportioned signal with the threshold signal; and
    means for generating an output signal whenever said proportioned signal exceeds the threshold signal.

11. The apparatus as defined in claim 10, including:
    means for setting the proportionality factor equal to the ratio between a peak value and the arithmetic average value of a full-wave rectified sinusoidal signal.

* * * * *